us008317811B2

United States Patent
Laporte Rosello et al.

(10) Patent No.: US 8,317,811 B2
(45) Date of Patent: Nov. 27, 2012

(54) SURGICAL INSTRUMENT FOR ENDOSCOPIC SURGERY

(75) Inventors: Enric Laporte Rosello, Sabadell (ES); Antonio Pena Gonzalez, Sabadell (ES); Jordi Carrera Fabra, Sabadell (ES); Albert Tomas Justribo, Sabadell (ES)

(73) Assignee: Corporacio Sanitaria Parc Tauli, Sabadell (ES)

( * ) Notice: Subject to any disclaimer, the term of this patent is extended or adjusted under 35 U.S.C. 154(b) by 543 days.

(21) Appl. No.: 12/281,614

(22) PCT Filed: May 24, 2006

(86) PCT No.: PCT/ES2006/000284
§ 371 (c)(1),
(2), (4) Date: Jan. 19, 2009

(87) PCT Pub. No.: WO2007/099175
PCT Pub. Date: Sep. 7, 2007

(65) Prior Publication Data
US 2009/0222022 A1 Sep. 3, 2009

(30) Foreign Application Priority Data
Mar. 3, 2006 (ES) .................................. 200600522

(51) Int. Cl.
*A61B 17/94* (2006.01)
(52) U.S. Cl. ............................................ 606/170; 606/1
(58) Field of Classification Search .................. 600/101, 600/137, 139, 141, 142, 146; 606/205, 207, 606/170, 174
See application file for complete search history.

(56) References Cited

U.S. PATENT DOCUMENTS

| | | | |
|---|---|---|---|
| 3,557,780 A * | 1/1971 | Sato ............................... | 600/141 |
| 3,572,325 A * | 3/1971 | Bazell et al. ................... | 600/141 |
| 4,178,920 A | 12/1979 | Cawood, Jr. et al. | |
| 5,209,747 A | 5/1993 | Knoepfler | |
| 5,366,479 A | 11/1994 | McGarry et al. | |

(Continued)

FOREIGN PATENT DOCUMENTS
EP 0592243 4/1994
(Continued)

OTHER PUBLICATIONS

International Search Report, dated Oct. 23, 2006, issued in International Application No. PCT/ES2006/000284.

*Primary Examiner* — Ryan Severson
*Assistant Examiner* — Rachel S Papeika
(74) *Attorney, Agent, or Firm* — Nixon Peabody LLP

(57) ABSTRACT

Surgical instrument for endoscopic surgery that permits the simulation of the articulation movements of a surgeon finger, comprising a rigid tube (3) whose distal end has a first phalanx (4) articulated, being in turn articulated to a second phalanx (5), which is linked to the rigid tube (3) by means of cables housed in cross ducts (12), situated in the interior of the first phalanx (4), linking the movement of the second phalanx (5) to that of the first phalanx (4), whose articulation takes place due to the actuation of the transmission rod (11), the rigid tube (3) being attachable to a handle (1) that incorporates a controller (2) for the actuating of the instrument articulation movement by the surgeon, which operates a fork (14), which in turns actuates the transmission rod (11).

19 Claims, 2 Drawing Sheets

U.S. PATENT DOCUMENTS

| | | | |
|---|---|---|---|
| 5,374,277 A * | 12/1994 | Hassler | 606/207 |
| 5,575,799 A * | 11/1996 | Bolanos et al. | 606/139 |
| 5,662,587 A * | 9/1997 | Grundfest et al. | 600/114 |
| 6,063,098 A * | 5/2000 | Houser et al. | 606/169 |
| 6,270,508 B1 | 8/2001 | Klieman et al. | |
| 7,025,064 B2 * | 4/2006 | Wang et al. | 128/898 |
| 7,850,600 B1 * | 12/2010 | Piskun | 600/114 |
| 7,963,976 B2 | 6/2011 | Goldfarb et al. | |
| 7,976,559 B2 | 7/2011 | Goldfarb et al. | |
| 2005/0107667 A1 * | 5/2005 | Danitz et al. | 600/139 |
| 2007/0152014 A1 * | 7/2007 | Gillum et al. | 227/175.1 |
| 2009/0171151 A1 * | 7/2009 | Choset et al. | 600/114 |

FOREIGN PATENT DOCUMENTS

| | | |
|---|---|---|
| EP | 0600182 | 6/1994 |
| ES | 2114962 | 6/1998 |
| WO | WO 94/21179 | 9/1994 |
| WO | WO 01/28431 | 4/2001 |
| WO | WO 2004/112845 | 12/2004 |

* cited by examiner

SURGICAL INSTRUMENT FOR ENDOSCOPIC SURGERY

Related Applications

This application is a U.S. National Phase of International Application No. PCT/ES2006/000284, filed May 24, 2006, designating the U.S. and published on Sep. 7, 2007 as WO 2007/099175, which claims priority to Spanish Patent Application No. P200600522. The content of this application is incorporated herein by reference in its entirety.

OBJECT OF THE INVENTION

The present invention refers to a surgical instrument for endoscopic surgery which has its application in the field of medicine, and more specifically in those operations connected with endoscopic surgery in which an instrument is required that is capable of executing a double articulation in an element inserted in the interior of the body cavity of a patient in a precise way controlled simply with just one hand by a surgeon.

BACKGROUND OF THE INVENTION

In the field of medicine, the endoscopic approach route has now become consolidated for performing intra-cavity operations, which offers numerous advantages over the open surgery techniques used traditionally. Endoscopy, which comprises the visual examination of a cavity or duct of the organism, is usually applied as a technique that minimizes the invasion of the patient's body cavity and is carried out by means of the insertion of an endoscope by way of a minimal surgical incision through which the sheath passes housing the instrument. The incorporation of cold light and a video camera enables therapeutic manoeuvres to be carried out in the abdominal cavity, ranging from the simple collection of a biopsy to complete operations on the organs that it contains.

In the abdomen, the introduction of the endoscope and the instruments is usually done by way of rigid or semi-rigid sheaths that pass through the abdominal wall. During the operation they facilitate the replacement of the instruments without the loss of the gas that is used to keep the cavity distended, thanks to a built-in valve system.

Similarly, in the particular case of laparoscopic surgery, i.e. that endoscopic technique used for actuation in the abdominal cavity, the use of surgical instruments is normally required for the dissection by the surgeon of anatomical spaces of loose conjunctive tissue, for which different types of tweezers and separators are also used.

The design of instruments of this type to perform a surgical operation by endoscopy is usually determined by a series of functional requirements that the instrument has to be able to fulfil, such as manipulation in the body cavity from the exterior, permitting internal actuation on organs or tissues. For this purpose, these instruments must be capable of performing a series of movements controlled by the surgeon from the exterior. The handling of the instruments in these conditions reduces the operator's manoeuvring capability since he is unable to guide the instrument grasped in his hand, making use of all the joints of his upper limb. The point of penetration of the cannula through which the instrument is inserted into the cavity restricts its movement in the same way as an oar in relation to the rowlock that secures it to the hull of the boat.

Accordingly, there is a tendency to incorporate articulated instruments that facilitate surgical manoeuvre instead of or as a supplement to traditional rigid instruments. These articulated instruments have different technical features depending on the surgery in which they are used and some of them are described below.

In U.S. Pat. No. 4,178,920, held by the institution 'American Hospital Supply Corporation', a urological instrument is defined that comprises a swivel element for use in cystoscopies, controlled manually by the operator, and which has a single element susceptible to be articulated for facilitating the introduction of a catheter in the mouth of a ureter. This instrument has a very limited application, since it is no use for dissection in spaces of difficult access or for those cases in which an instrument is required that simulates the movement that would be made by the surgeon's finger in open surgery operations. In addition, the articulated element is controlled directly, with no means of cushioning, so that the precision in the control of its movement is not very high, with the result that it proves rather rudimentary.

On the other hand, U.S. Pat. No. 5,366,479, applied for by the institution 'United States Surgical Corporation', describes another type of instrument used in endoscopy, which consists of a surgical stapler which, as in the previous case, has an area for gripping it, in the form of a handle, while coupled to this area there is a hollow rod-like element which has an articulated element at its free end that has its rotation in relation to an axis permitted in both directions. This instrument is used in surgery for applying staples, which are housed in a space in the interior of said hollow rod.

Now, although this instrument permits the rotation of the articulated element in both directions on account of its technical features and its configuration, it presents the same problems as the above-mentioned instrument, as it only permits a rotation movement of the swivel element, i.e. it only comprises one articulation and its use is limited as its purpose is strictly that of setting lines of staples in place for the occlusion of a specific segment of the digestive tube.

DESCRIPTION OF THE INVENTION

The present invention refers to a surgical instrument for endoscopic surgery which permits the execution of movements that emulate those performed by a surgeon's finger in open surgery operations, by means of a double articulation, all this in an easy and precise way, controlled simply by the surgeon with just one hand, in order to obtain, for instance, the mechanical emulation of the movements of dissection of anatomical spaces of loose conjunctive tissue.

In view of its features, the surgical instrument proposed by the invention has a special application in operations performed on both the upper and lower abdomen, using the endoscopic route. In the case of operations on the upper abdomen it is applicable, for example, in cholecystectomy or in gastroesophageal fundoplicature, in gastrectomy or in nephrectomy. In the case of operations on the lower hemiabdomen, the instrument is used to carry out the dissection of the preperitoneal space in the repair of a inguinal hernia, in iliac lymphadenectomy or in prostatectomy, for which the instrument is required to emulate the movements of a finger, so that it is best for these to be performed mechanically on account of the recurrence of the gestures.

In order to meet the above-mentioned functional requirements, the instrument that is the object of the invention comprises a handle, which has an appropriate configuration for it to be gripped and handled by the surgeon with just one hand. Attached to it there is a rigid tube, which is the invasive part of the instrument, at the distal end of which it has a first phalanx articulated in relation to the end of said rigid tube. Said first phalanx has, in turn, a second phalanx articulated at its distal end, the articulation movement of the second phalanx being linked to the articulation movement of the first phalanx by means of cables housed in cross ducts, emulating in this way the articulation movement of a human finger.

The instrument is held by the handle with a single hand, being controlled by means of placing preferably two fingers, such as for instance the index and middle finger, on a controller located in an area adjacent to the handle, in the form of a trigger, on which an axial movement may be made either by pulling or pressing said controller.

The interior of the handle holds at least a spring, or some other equivalent cushioning element that regulates and increases the precision of the movement of the controller, which actuates an operating fork, which in turn actuates a transmission rod, which undergoes linear forward movement, said transmission rod being connected to a link, which is in turn connected by its opposite end to the first phalanx.

In this way, when the surgeon actuates the controller, this operates the transmission rod by way of the fork, causing it to make a linear forward movement inside the rigid tube, while at the same time operating in turn the end of the transmission rod and the link, which is what produces a bending movement in the first phalanx, which swivels in relation to a first axis of rotation.

The movement of a second phalanx takes place as a result of the swivel movement of the first phalanx on account of the connection that exists between them, so the second phalanx cannot execute a movement separately from the first phalanx, i.e. without this being articulated. The instrument therefore comprises the disposition of cables linking the area of the distal end of the rigid tube, in which these are fixed by means of anterior anchoring holes, with the area of the proximal end of the second phalanx, in which they are fixed by means of end anchoring holes, said cables being crossed by means of cross ducts located in the interior of the first phalanx.

By means of the cross cable ducts the second phalanx is successfully connected to the first phalanx, with the result that the movement of this produces a relative movement of the second phalanx in relation to the first phalanx, so that an articulation takes place in respect of a second axis of rotation, located at the distal end of the first phalanx, produced by the actuation of the cables situated on the opposite side to the direction of rotation, which, through being crossover, produces an actuation on the side of the direction of rotation of the second phalanx, acting inversely when the first phalanx recovers its non-articulated position, which constitutes a movement that emulates the articulation movement performed by the phalanxes of a human finger.

Furthermore, in order to endow the instrument with a superior precision and range of positions, which affords it a greater versatility, the whole rigid tube is provided with the possibility of turning from its position on its own axis in relation to the fixed portion or handle. This is achieved by means of a rotation crown which is situated in the area of the handle provided for the attachment of said rigid tube. The possibility is contemplated of having a mechanism in the interior of said rotation crown comprising at least a spring, or some other equivalent means of cushioning, which permits the rigid tube to be locked or unlocked in a given position after being turned, at the surgeon's discretion, so that said rigid tube, which can turn through 360°, is endowed with complete freedom of rotation while maintaining all the functions and capabilities of the instrument.

The possibility is also contemplated of having an initial positioning or neutral wheel in the area of actuation of the fork with the transmission rod. By turning it we can adjust its position in relation to the transmission rod, so that, given the position of the fork in respect of said initial positioning wheel, we achieve a given initial position in which the first phalanx and the second phalanx are articulated prior to the operation of the controller by the surgeon, when so required for a specific process.

In this way, the initial or neutral position of the first phalanx and of the second phalanx may be kept perfectly straight, without any articulation of same, or else an initial position of said phalanxes of the instrument with a given articulation; it is even possible to achieve the initial position, without acting on the controller, with a given articulation when the instrument is in the interior of the patient's body cavity, without the need to withdraw it, which proves extremely useful during the course of an operation.

In order to increase the versatility of the instrument, as a variant the possibility is considered of providing an internal axial hole both in the rigid tube and in the first and second phalanx, which are connected to a duct in order to enable the tasks of irrigation and suction of liquids to be performed during surgery. The option is also contemplated of incorporating an electric or ultrasound scalpel, of the types known in the state of the art, at the distal end of the second phalanx, so that it may be used in such processes as haemostasis.

In the instrument that is the object of the invention it is considered incorporating elements that will enable it to be operated remotely, i.e. that allow it to be used from a distance, in telesurgery operations. For this the action of the forces exerted by the surgeon is replaced by a robot, providing the distal end of the rigid tube with sensors, which may consist of the disposition of extensiometric gauges according to the three axes of three-dimensional space. Thus, they convert the forces that act on the instrument into electrical signals, providing information on the forces acting on the instrument, or else on the forces that the instrument is exerting on the patient, similar to the perception that the surgeon's hand would have if the instrument were being handled by him. This enables the magnitude of the forces and the direction of the movements made by the instrument to be regulated at all times.

Therefore, in accordance with the invention described, the surgical instrument for endoscopic surgery proposed by the invention represents an advance in the instruments for endoscopic surgery used heretofore and it resolves the problems explained above in a fully satisfactory way, in that it is a versatile instrument that is provided with a double articulation in order to permit access and its simple precise actuation from the exterior in those areas of the body cavity which are of difficult access in endoscopy, simulating the articulation of a human finger and facilitating a wide variety of movements of the invasive part of the instrument without the need to withdraw it from the patient's body cavity during the course of the operation.

DESCRIPTION OF THE DRAWINGS

In order to supplement the description being given and to assist a clearer understanding of the features of the invention, in accordance with a preferred specimen practical embodiment of the same, we adjoin as an integral part of said description, a set of drawings wherein there is represented, for informative and non-restrictive purposes, the following.

PREFERRED EMBODIMENT OF THE INVENTION

Figure 1:
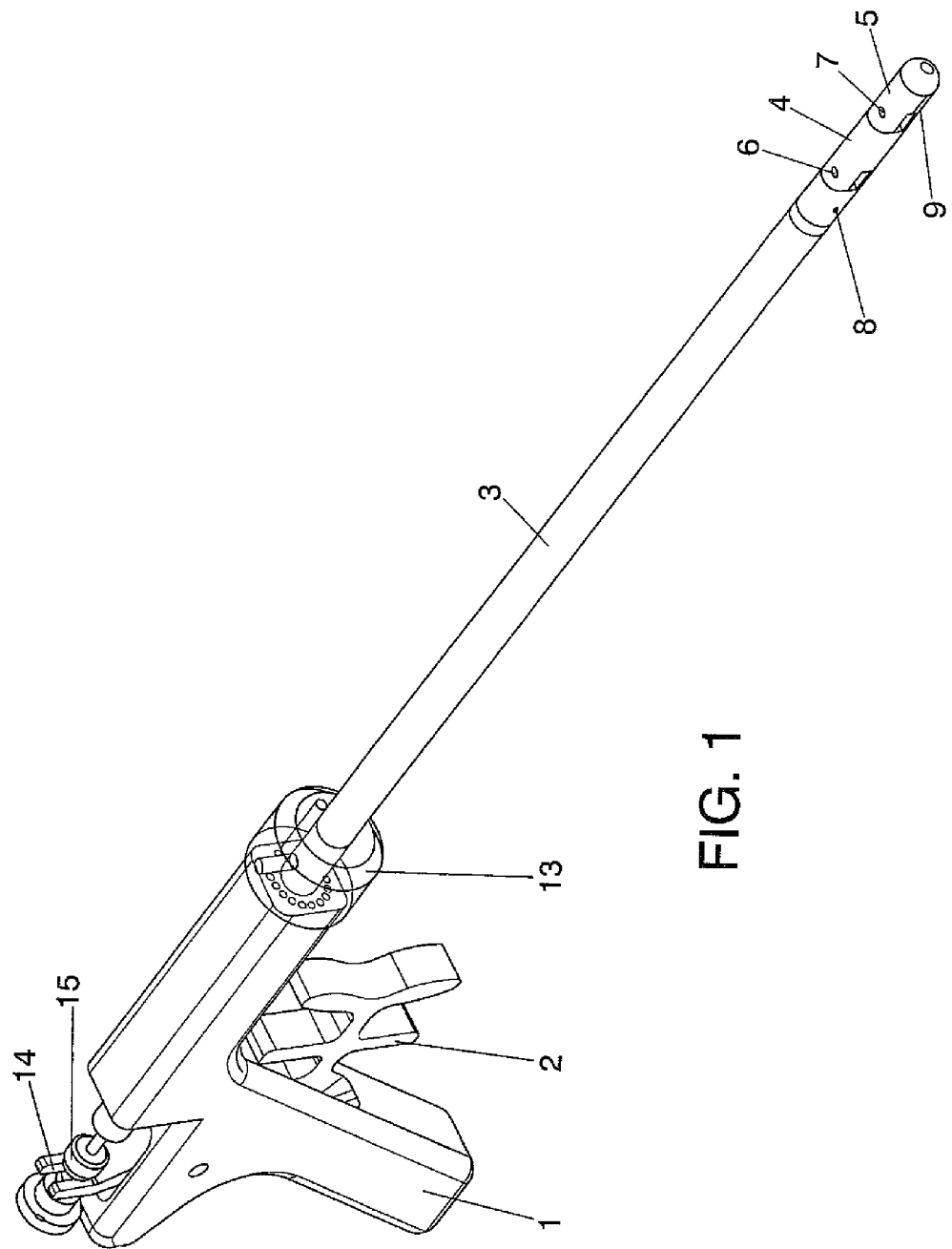
FIG. 1. It shows a perspective view of the surgical instrument for endoscopic surgery that is the object of the invention.
Figure 2:
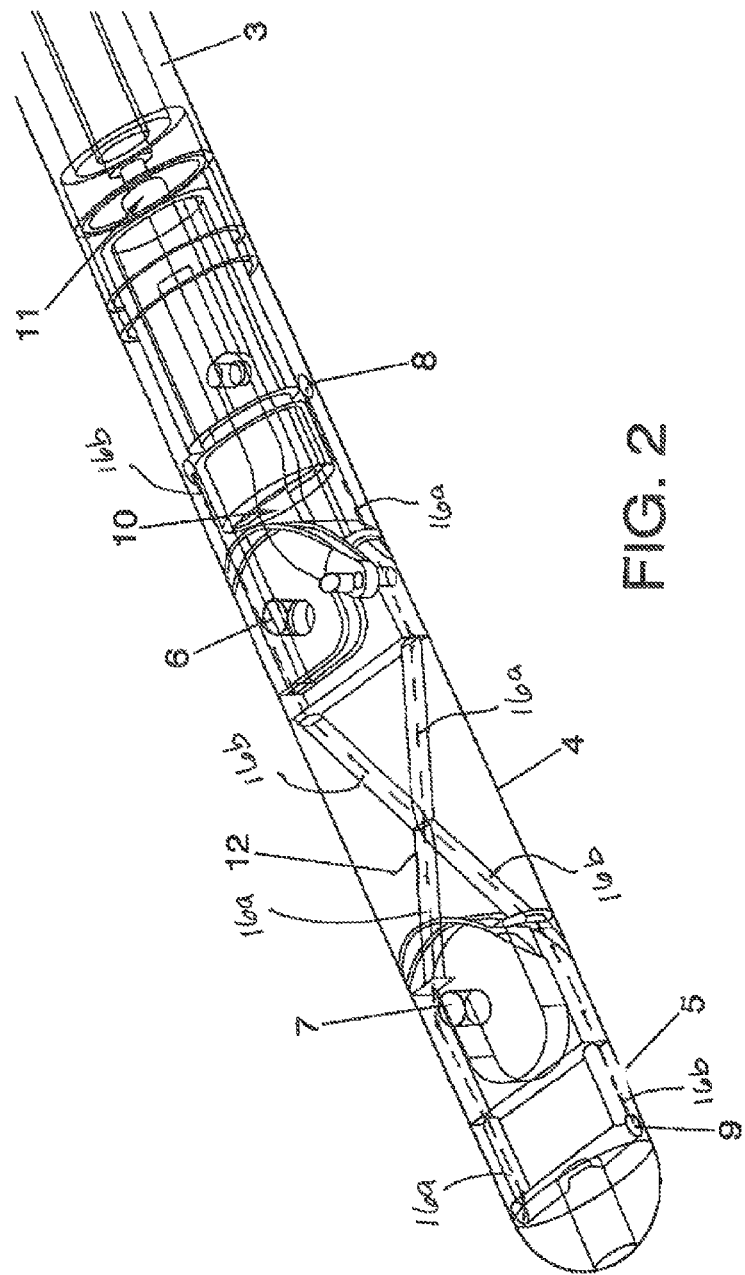
FIG. 2. It shows a perspective view, in which the outer surfaces are represented as transparent in order to show the interior elements, in which we may observe a close view corresponding to the end area of the rigid tube as well as the first phalanx and the second phalanx of the instrument.

In the light of the afore-mentioned figures, it may be observed how in one of the possible embodiments of the invention, the surgical instrument for endoscopic surgery comprises a rigid tube (3), the distal end of which has a first phalanx (4) articulated in relation to a first axis of rotation (6), which, in turn, at its distal end, has a second phalanx (5) articulated in respect of a second axis of rotation (7).

The interior of the rigid tube (3) houses a transmission rod (11), which is connected at its distal end to a link (10), which in turn is also connected, by its opposite end, to the first phalanx (4), the actuation of this transmission rod (11) being what produces the articulation of the phalanxes (4) and (5) of the instrument.

The movement of the second phalanx (5) is linked to that of the first phalanx (4) by means of cables (16a and 16b) housed in cross ducts (12) situated in the interior of the first phalanx (4), which are fixed at the distal end of the rigid tube (3) by means of anterior anchoring holes (8), and at the proximal end of the second phalanx (5) by means of end anchoring holes (9).

The rigid tube (3) is attachable to a handle (1), which has a suitable configuration for the holding, gripping and handling of the instrument by the surgeon with only one hand. It has a controller (2), which, when operated, usually with the fingers, actuates a fork (14), which in turn actuates the transmission rod (11) for its operation.

The possibility is contemplated of having in the interior of the handle (1) at least a spring—not represented—or some other equivalent cushioning element, which regulates and increases the precision of the movement of the controller (2).

Furthermore, in order to endow the instrument with a superior precision and range of positions, the possibility is contemplated of permitting the turning of the rigid tube (3) on its own axis in relation to the handle (1) by means of a rotation crown (13), which is situated in the area of attachment between the handle (1) and the rigid tube (3).

The option is also considered of having in the interior of said rotation crown (13) a mechanism—not represented—comprising at least a spring, or some other equivalent means of cushioning, for locking the position of the rigid tube (3).

The possibility is also contemplated of having an initial positioning wheel (15) in the area of actuation of the fork (14) with the transmission rod (11), which permits the positional adjustment of the fork (14) in relation to the transmission rod (11), so that it permits the regulation of the initial position of articulation of the first phalanx (4) and of the second phalanx (5), prior to the operation of the controller (2) by the surgeon.

As a variant, the possibility is also considered of providing an internal axial hole both in the rigid tube (3) and in the first phalanx (4) and in the second phalanx (5), which permit their connection to a duct—not represented—in order to enable the tasks of irrigation and suction of liquids to be performed during surgery.

The option is also contemplated of incorporating the terminal of an electric or ultrasound scalpel, of the types known in the state of the art, at the distal end of the second phalanx (5), so that it may facilitate electrocoagulation haemostasis with the same instrument.

In the instrument, consideration is also given to incorporating elements that will enable it to be operated remotely in telesurgery operations, permitting the forces exerted by the surgeon for the actuation of the instrument to be applied by a robot, providing the distal end of the rigid tube (3) with sensors, which may consist of extensiometric gauges according to the three axes of three-dimensional space, which convert the forces that act on the instrument into electrical signals, providing information on the forces that the instrument is exerting on the patient, thus enabling the magnitude of the forces and the direction of the movements made by the instrument to be regulated at all times.

The possibility is also considered of its being disposable and being made with the intention of its being used in one operation only. In this case the instrument would be sealed, not permitting its disassembly and therefore not permitting its correct resterilization for reuse.

In the light of this description and set of figures, an expert on the matter would be able to appreciate that the embodiments of the invention which have been described may be combined in numerous ways within the object of the invention. The invention has been described according to some preferred embodiments of same, but for an expert on the matter it will be evident that multiple variations may be introduced in said preferred embodiments without exceeding the object of the invention claimed.

The invention claimed is:

1. A surgical instrument for endoscopic surgery that comprises an elongate rigid tube having a proximal end portion and a distal end portion, a first phalanx having a proximal end and a distal end, a second phalanx having a proximal end, the proximal end of the first phalanx coupled with the distal end portion of the elongate rigid tube in a manner that permits the first phalanx to pivot with respect to the elongate rigid tube, the proximal end of the second phalanx coupled with the distal end of the first phalanx in a manner that permits the second phalanx to pivot with respect to the first phalanx, the second phalanx linked to the rigid elongate tube by first and second cable segments, the first and second cable segments each comprising a proximal end portion, a distal end portion and an intermediate portion extending between the proximal and distal end portions, the proximal end portions of the first and second cable segments fixed to the elongate rigid tube, the distal end portions of the cable segments coupled to an interior of the second phalanx, the intermediate portion of the first cable segments positioned within a first duct situated in an interior of the first phalanx, the intermediate portion of the second cable segment positioned within a second duct situated in the interior of the first phalanx, the intermediate portion of the first cable segment having a freedom of movement within the first duct, the intermediate portion of the second cable segment having a freedom of movement within the second duct, the first and second ducts oriented within the first phalanx so that the intermediate portions of the first and second cable segments cross one another within the interior of the first phalanx, the first and second cable segments linking the pivotal movement of the second phalanx to the pivotal movement of the first phalanx.

2. A surgical instrument according to claim 1, further comprising a first set of anchoring holes in the elongate rigid tube by which the proximal end portions of the first and second cable segments are fixed to the elongate rigid tube, and a second set of anchoring holes in the second phalanx by which the distal end portions of the first and second cable segments are fixed to the second phalanx.

3. A surgical instrument according to claim 1, further comprising a transmission rod located and moveable between a first axial position and a second axial position in the interior of the elongate rigid tube, the transmission rod having a proximal end and a distal end, the distal end of the transmission rod connected to a link, which is configured to operably engage the first phalanx to cause the first phalanx to pivot with respect to the elongate rigid tube upon the transmission rod being axially moved between the first axial position and the second axial position within the elongate rigid tube.

4. A surgical instrument according to claim 3, further comprising a handle assembly coupled to the proximal end portion of the elongate rigid tube, the handle assembly having a configuration for the holding, gripping and handling of the instrument with one hand.

5. A surgical instrument according to claim 4, wherein the handle assembly comprises a controller that operates a fork, which in turn acts on the transmission rod to move the transmission rod between the first and second axial positions.

6. A surgical instrument according to claim 5, wherein the handle assembly comprises an internal spring, or other resilient element, for regulating and increasing the precision of the movement of the controller.

7. A surgical instrument according claim 5, wherein the first axial position of the transmission rod is adjustable for regulating the initial rotational position of the first phalanx and of the second phalanx.

8. A surgical instrument according to claim 4, wherein the elongate rigid tube is enabled to rotate around its own axis in respect of the handle assembly by a rotation crown which is situated in an area between where the handle assembly and the rigid tube are coupled.

9. A surgical instrument according to claim 8, wherein the rotation crown houses a mechanism comprising at least a spring, or other resilient member, for locking the position of the rigid tube.

10. A surgical instrument for endoscopic surgery comprising:
an elongate member having a first internal lumen, a proximal end portion and a distal end portion;
a first phalanx having a proximal portion and a distal portion, the proximal portion pivotally coupled to the distal end portion of the elongate member about a first pivot axis;
a rigid transmission member having a proximal end portion and a distal end portion, the rigid transmission member positioned in the first internal lumen of the elongate member, the distal end portion of the rigid transmission member operatively coupled to the proximal portion of the first phalanx, the proximal end portion of the rigid transmission member operatively coupled to an actuator positioned near the proximal end portion of the elongate member, the rigid transmission member moveable within the first internal lumen between a first axial position and a second axial position by operation of the actuator to cause the first phalanx to rotate about the first pivot axis between a first angular position and a second angular position;
a second phalanx having a proximal portion and a distal portion, the proximal portion of the second phalanx pivotally coupled to the distal portion of the first phalanx about a second pivot axis;
first and second cable segments each having a proximal end portion, a distal end portion and an intermediate portion extending between the proximal and distal end portions, the first end portions being fixed to the distal end portion of the elongate member proximal to the first pivot axis, the second end portions being fixed to the second phalanx distal to the second pivot axis, the intermediate portions intersecting and extending through at least a portion of the first phalanx;
the first phalanx acts upon at least one of the intermediate portions of the first and second cable segments upon rotating between the first angular position and the second angular position to cause the second phalanx to rotate about the second pivot axis.

11. A surgical instrument according to claim 10, wherein the first phalanx comprises guide members that cause the intermediate portions of the first and second cable segments to assume their intersecting relationship within the first phalanx.

12. A surgical instrument according to claim 11, wherein the guide members are cross ducts situated within the interior of the first phalanx.

13. A surgical instrument according to claim 10, wherein the proximal end portions of the first and second cable segments are coupled to opposing sides of the first internal lumen.

14. A surgical instrument according to claim 10, wherein the elongate member, first phalanx and second phalanx comprise a first, a second and a third longitudinal axis, respectively, the proximal end portion of the first cable segment and the proximal end portion of the second cable segment coupled within the elongate member at different angular positions with respect to the first longitudinal axis, the distal end portion of the first cable segment and the distal end portion of the second cable segment coupled within the second phalanx at different angular positions with respect to the third longitudinal axis.

15. A surgical instrument according to claim 10, wherein the first cable segment and the second cable segment are operably positioned within the first phalanx and the second phalanx to cause the first phalanx and second phalanx to pivot in unison and in the same rotational direction upon the transmission member being moved between the first and second axial positions.

16. A surgical instrument according to claim 10, further comprising first and second ducts extending through at least a portion of the first phalanx, the first phalanx having a first longitudinal axis with the first and second ducts intersecting one another along the first longitudinal axis, the intermediate portion of the first cable segment extending through the first duct, the intermediate portion of the second cable segment extending through the second duct.

17. A surgical instrument according to claim 16, wherein the elongate member and second phalanx comprise a second and a third longitudinal axis, respectively, the proximal end portion of the first cable segment and the proximal end portion of the second cable segment coupled within the elongate member at different angular positions with respect to the second longitudinal axis, the distal end portion of the first cable segment and the distal end portion of the second cable segment coupled within the second phalanx at different angular positions with respect to the third longitudinal axis.

18. A surgical instrument according to claim 10, wherein the elongate member is rigid.

19. A surgical instrument according to claim 10, wherein the elongate member is a rigid tube.

* * * * *